(12) United States Patent
Lequeux

(10) Patent No.: US 12,051,502 B2
(45) Date of Patent: Jul. 30, 2024

(54) HEALTHCARE DATA CLOUD SYSTEM, SERVER AND METHOD

(71) Applicant: Blayne Lequeux, Dana Point, CA (US)

(72) Inventor: Blayne Lequeux, Dana Point, CA (US)

( * ) Notice: Subject to any disclaimer, the term of this patent is extended or adjusted under 35 U.S.C. 154(b) by 693 days.

(21) Appl. No.: 16/849,312

(22) Filed: Apr. 15, 2020

(65) Prior Publication Data

US 2021/0043319 A1    Feb. 11, 2021

Related U.S. Application Data

(60) Provisional application No. 62/847,469, filed on May 14, 2019.

(51) Int. Cl.
*G16H 40/67* (2018.01)
*G16H 10/60* (2018.01)

(52) U.S. Cl.
CPC ............. *G16H 40/67* (2018.01); *G16H 10/60* (2018.01)

(58) Field of Classification Search
CPC ............................... G16H 40/67; G16H 10/60
See application file for complete search history.

(56) References Cited

U.S. PATENT DOCUMENTS

| | | | | |
|---|---|---|---|---|
| 2007/0299697 A1* | 12/2007 | Friedlander | ........... | G16H 10/60 705/3 |
| 2009/0024589 A1 | 1/2009 | Sood et al. | | |
| 2010/0169348 A1* | 7/2010 | Maro | ............... | G06F 16/24556 707/E17.014 |
| 2012/0102002 A1 | 4/2012 | Sathyanarayana et al. | | |
| 2015/0358219 A1* | 12/2015 | Kanda | ................ | H04L 41/0896 709/224 |
| 2016/0154859 A1 | 6/2016 | Skurtovich, Jr. et al. | | |
| 2017/0054591 A1* | 2/2017 | Hyoudou | .............. | H04L 45/583 |
| 2018/0210926 A1* | 7/2018 | Schulze | ............... | G06F 16/258 |
| 2020/0051668 A1* | 2/2020 | Zoia | ....................... | G16B 30/20 |

FOREIGN PATENT DOCUMENTS

KR    10-2016-0059294 A    5/2016

OTHER PUBLICATIONS

Korean Intellectual Property Office; Patent Cooperation Treaty International Search Report and Written Opinion, issued in connection to PCT/US2020/028274; Jul. 27, 2020; 13 pages; South Korea.

* cited by examiner

*Primary Examiner* — Jay M. Patel
(74) *Attorney, Agent, or Firm* — Greenberg Traurig, LLP

(57) ABSTRACT

In some embodiments, the system integrates different unique identifiers from agencies and organizations and associated the different unique identifiers with each other in a table. In some embodiments, the table links all different unique identifiers to a single individual so that a search for any one identifier returns links to all records and data associated with the individual. In some embodiments, the system collects the different unique identifiers from organizations such as patient medical services, local and federal law enforcement databases, and private company records. In some embodiments, the system parses each component of each identifier and stores them as variations. In some embodiments, each parsed identifier is associated with a master identifier. In some embodiments, the system links the master identifier to all records and data across multiple organizations and agencies.

7 Claims, 6 Drawing Sheets

HEALTHCARE DATA CLOUD SYSTEM, SERVER AND METHOD

CROSS-REFERENCE TO RELATED APPLICATIONS

This application claims the benefit of and priority to U.S. Provisional Application No. 62/847,469, filed May 14, 2019, entitled "Healthcare Data Cloud System, Server and Method", the entire contents of which are incorporated herein by reference.

BACKGROUND

There have been revolutionary advancements in data gathering over the last century. Today, multiple organizations keep troves of records about an individual's preferences and history. The most common practice is to associate each record with a unique identifier, such as the person's name, so that a search for that unique identifier retrieves all associated records. This record retrieval is sometimes performed across multiple databases. However, different databases made by different software manufactures are not always compatible, and do not always communicate with each other. This can cause major problems, especially in the healthcare industry.

Even systems that do communicate with each other, such as healthcare and law enforcement databases, are not always able to properly identify an individual due to various names used as identifiers at different times and/or across different databases. Name variations that refer to the same individual might be the result of a name change after a marriage, might result from the use of middle names and nicknames as part of the identifier, might be from mistakes made from manual data entry, may be from the sale or restructuring of a corporation, etc.

To exacerbate the problem, there are countless individuals that have the same name. To combat confusion, prior art systems typically associate a person's name with additional identifying information such as an address, a driver's license number, a social security number, a telephone number, or some other unique identifier. A problem that exist currently in the art is that there is no consistency: one prior art system may use one additional identifier type, while another system may choose to use a different type. Changes in an individual's address, telephone number, or a driver's license number, can also cause breaks in record links as not all databases are updated when a unique identifier has changed.

Compounding problems with record retrieval even further, a system of updating unique identifiers across multiple industries has not yet been achieved due to privacy concerns. Some system databases do not allow access to records where the name and corresponding identifying information is not an exact match. Some databases do not allow outside access for any reason. However, the identification variations that hold the key to linking multiple records across different industries is currently locked away in distributed systems.

Healthcare professionals are issued CMS National Provider Identifier (NPI) numbers; however, organizations can have many NPIs. Providers are notorious for not maintaining their demographic data current. In addition, every person uses multiple identifiers. While Social Security Numbers are a unique identifier for an individual, Social Security Numbers are illegal for general use in healthcare. Furthermore, millions of people are not identified or do not want to be identified and many providers submit claims through different identities. All health plans have their own patient and provider identifiers which are linked to claims.

In conventional methods, business and accounting processes are managed by thousands of paper and computer systems, which cannot attempt to relate hundreds of millions of varying identifiers for providers, patients and service organizations. In these conventional systems, names are entered into computers from handwritten forms or verbal spellings as well as addresses and phone numbers.

The average health plan member creates about a dozen claims per year and each claim is reviewed by dozens of plan functions and ancillary organizations with a financial interest in the claim. Each plan member's claims are reviewed 3 to 5 times creating approximately billions of identification events per year. Even if all identifiers were accurately recognized the overhead burden is significant. If an identification error occurs anywhere in the adjudication process then the claim is pended for review, identification and reprocessing. It is common in healthcare for bills to be sent multiple times due to processing lag, identification errors, reprocessing and late payment cycles.

The lack of a comprehensive identification system has let to massive fraud and abuse as well as overutilization cost. An investigation of a chiropractor found that he operated under a personal NPI and 3 corporate NPIs and prescribed $8M in compounded drugs which included narcotics and $22M through his company which were all paid legally. The person and the company were shut down but kept the money. A major health plan paid all podiatrists' claims for years and then determined that about 1,000 were prescribing compounded drugs with narcotics costing the plan $65M per year. The Federal government issues DEA numbers for prescribers but stopped managing the process years ago. Now almost anybody in healthcare can prescribe any drug. These are all example identification problems with high cost impact.

Reimbursement for healthcare services offered to 300+ million people in the US, provided by 15 million medical professionals and organizations, supported by 10 million workers in insurance, administrative and ancillary services organizations have surpassed $3.6 trillion annually. Conservative estimates assign over 28% ($1 Trillion) in losses every year to fraud, waste and abuse. The vast majority of efforts to stem these losses require accurate reference data as an imperative. Table A below shows current healthcare segments and their corresponding segment percentage and projected participants.

TABLE A

| Healthcare Segments | Segment Percentage | Projected Participants |
| --- | --- | --- |
| Employer | 49% | 163,660,000 |
| Non-Group | 6% | 20,040,000 |
| Medicaid | 20% | 66,800,000 |
| Medicare | 14% | 46,760,000 |
| Military | 1% | 3,340,000 |
| Uninsured | 9% | 30,060,000 |
| 2021 Total USA | | 334,000,000 |

Therefore, there is a need for a system that is able to identify an individual and/or agency by using any combination of unique identifiers used by distributed systems and associate each variation with all the distributed systems' records.

SUMMARY

Some embodiments of the Healthcare Data Cloud System, Server and Method (hereafter the "system") includes systems and methods of identifying individuals, patients, employees, entities, corporations, products, structures, landmarks, computer programs, and/or anything that can be identified by a proper name (hereafter an/the "individual" and/or "individuals"). In some embodiments, the system identifies individuals by collecting, storing, analyzing, processing, and publishing multiple variations of identifying information associated with an individual. In some embodiments, the system associates one or more of those variations with the distributed systems' records.

In some embodiments, the system includes a cloud-based reference service provided through a computer-to-computer function called a web service that automatically reviews and uniquely identifies all parties to a healthcare transaction or claim. In some embodiments, this Web service is callable by any Web-connected administrative system using a function that submits one or more transactions which are identified, and correct identifiers and verified names and demographic data are appended to each record in milliseconds per record. In some embodiments, if a record cannot be automatically identified, it is pended, and a reviewer resolves and releases the record to the client. In some embodiments, identities may be manually researched by an individual in a Web browser.

In some embodiments, the system includes Service Offerings. In some embodiments, Comprehensive Data-as-a-Service (DaaS) Web services are configured for accepting a single entry or batch file to find a person, organization, or healthcare provider (professional or institution) and return a fixed format response. In some embodiments, the system includes Basic and smart DaaS APIs configured to help customers answer a variety of commercial questions.

In some embodiments, the system includes a Learning Database. In some embodiments, a Learning Database retains variations of identifiers (e.g., individuals, organizations, relationships, and/or addresses). In some embodiments, the system includes a learning database technology that records variations of a name of an individual, entity, organization, address and other defining attributes. In some embodiments, the system is configured to store variable data in a proprietary variations database. In some embodiments, a variations database (e.g., a variations table) is used for identification and managed by the system via a logic system and rules tables. In some embodiments, individuals, organizations and addresses that cannot be automatically identified may be resolved through other data sources or manually. In some embodiments, the system is configured such that the frequency of names matches for master and errata names are recorded and the source data of each change is recorded along with the date and time. In some embodiments, Unique IDs are stored for each address for an individual and organization along with the data source and date. In some embodiments, the rules match logic will be enhanced using system logic along with matching the individual person's identity to the professional provider identity.

In some embodiments, the system includes a web portal that offers a single-line entry to identify people, organizations, and healthcare institutions and providers by defining parameters such as geography, people demographics, etc. In some embodiments, the system is configured to allow users to design and produce reports and perform analyses incorporating statistics, sorting, artificial intelligence and graphic mapping displays.

In some embodiments, the system's AI and or machine learning is configured to learn through iterative use. In some embodiments, iterative use of the service enhances the system because the source data and logic for every edit is retained. In some embodiments, the web user interface is configured to guide the user through a process of finding information, answering questions, and adjusting the user interaction based on the experience history of the user. In some embodiments, the system is configured for source data maintenance using web services and automated, secure FTP sites to intake, process, edit, refine and load into the system to create the output of clean client data.

In some embodiments, the system includes one or more databases with data about people, organizations, locations, identifiers, demographics, and attributes. In some embodiments, the system includes a population database uniquely identifies millions (e.g., 285 million-plus) of individual people using multiple attributes (e.g., 400-plus attributes). In some embodiments, the system includes an organization database that uniquely identifies public, private, social, industry and governmental organizations (e.g., 20 million-plus agencies) with attributes (e.g., 300-plus attributes) and tracks related individuals. In some embodiments, the system includes an address database for addresses, misspellings, Lat and Lon, and other geographic definitions (e.g., for maintaining the 150 million-plus addresses in the USA).

In some embodiments, the system uses one or more of uniquely identifying information such as one or more current and/or past names, addresses, driver's license numbers, social security number, telephone numbers, pictures, computer readable code, fingerprints, retinal scans, biometric data, metadata (e.g., digital footprints such as driving patterns, purchase patterns, web browser history, etc.), public and/or private records, and/or any other type of identifier associated with an individual to confirm the individual's identity. In some embodiments, name variations can include nicknames, surnames, titles, given names, family names, aliases, user names, corporate names and/or any title an individual may use for identification purposes. Uniquely identifying information and the variation thereof are collectively referred to as an identifier(s), and/or an ID(s) herein.

In some embodiments the system is used by healthcare industries. In some embodiments, the system allows for different healthcare systems to communicate information about individuals. In some embodiments, different healthcare systems identify patients using different IDs. In some embodiments, the system creates a database including all the different IDs that has been associated with an individual. In some embodiments, advanced scouring tools are used to gather IDs from multiple online systems to create a database of IDs associated with an individual. In some embodiments, the system is shared by healthcare agencies, law enforcement agencies, government agencies, marketing agencies, and/or any individual, organization, or corporation (collectively referred to as an "agency" and/or "agencies"). In some embodiments, agencies use one or more identifiers to associate one or more documents, records, links, and/or data (collectively referred to as data) with a single individual. In some embodiments, the system is used by one or more agencies to identify an individual associated with multiple IDs.

In some embodiments, the system is configured for general use anywhere in the $4 trillion U.S. healthcare system. In some embodiments, the system is configured for tracking and identifying individuals during an epidemic to track the source and/or positively identify specific individuals who may have come into contact with each other. In some embodiments, the system is configured to compare records (e.g., credit card usage; phone records; entry logs; metadata) from one individual's ID to another individual's ID such that infected individuals can be tracked and/or notified. In some embodiments, the system if fully implemented by agencies would have helped mitigate the effects of the Corona Virus outbreak of 2020, for example.

Some embodiments include a system, server and method comprising at least one processor, and at least one non-transitory computer-readable storage medium in data communication with the at least one processor that is configured to store and exchange data comprising or representing data derived or received from at least one server of at least one data source, database, and/or at least one user. Some embodiments include an application programming interface (API) in data communication with the at least one processor and the at least one non-transitory computer-readable storage medium. In some embodiments, the application programming interface includes steps executable by the at least one processor to upload, download, or enable access of the content data derived or received from the at least one server of at least one healthcare data source and/or at least one user.

In some embodiments, one or more of: outpatient, inpatient, prescription, laboratory, dental and vision claims are retained in a cloud system. In some embodiments, the outpatient, inpatient, prescription, laboratory, dental and vision claims can be linked to patients, providers and health plans in a manner that facilitates one or more of the following: near real-time, bi-directional updating of data sources with a healthcare data cloud system master database; access to interactive web browsers for real-time and batch processes for queries, reports, analysis and research purposes; individuals making inquiries for claims, eligibility, health profiles, benefits, electronic medical records, questions and answers, finding in-network doctors, labs, outpatient facilities, pharmacies, and the like; analysis of provider networks, provider assessment, network optimization; and actuarial underwriting, claims modeling, analysis of group plans and loss-ratio projections.

In some embodiments, communication with the system occurs interactively through a web browser. In some embodiments, the system can use a natural language interface. In some embodiments, the natural-language interface allows a user to communicate with the system using common linguistic sentences, phrases, questions, and/or clauses to select, modify, and/or create data. In some embodiments, the healthcare data cloud system uses automated web services for computer-to-computer transactions. In some embodiments, automated web services allow software that may have different programming languages to communicate over a network (e.g., the World Wide Web). In some embodiments, application programming interfaces (APIs) enable communication between different types of software. In some embodiments, the system can use an automated and interactive file transfer protocol website. In some embodiments, one or more interactive file transfer protocol websites enable file uploads and downloads.

In some embodiments, the system includes a Natural Language Processing System (NLPS). In some embodiments, the system includes a Natural Language Variations Table (NLVT). In some embodiments, a Web page for user input and requests consists of a single line entry using natural language to query the system, produce reports, load and edit data and numerous other user functions. In some embodiments, the NLPS is focused on healthcare applications and terminology referring to medical diagnoses and procedures and terms applying to healthcare claims for outpatient and inpatient services. In some embodiments, if the user uses an unrecognized term the system will attempt to relate the entry to similar terms in the NLVT. In some embodiments, if relating the entry to similar terms in the NLVT is successful the system is configured to store the term for the user. In some embodiments, if relating the entry to similar terms in the NLVT is unsuccessful, the system is configured to enable manual entry of the term (e.g., the term is researched by a technician and new terms are added to the system). In some embodiments, the NLPS includes all data definitions and variations from the DIMU and DMU then into the NLVT. Reports and terms created in the RDMU are also incorporated into the NLVT and can be reference in a natural language user request. Individual names and organizations entered through the NLPS are recognized using the functions of the IMU and the related variations tables.

In some embodiments, the systems and data sets are designed to incorporate deep learning and artificial intelligence. In some embodiments, systems and data sets can give fast access and analysis of vast amounts of data. In some embodiments, systems and data sets can improve healthcare and healthcare costs. In order to meet these goals, some embodiments of the healthcare data cloud system are configured to respond to questions. In some embodiments, example input questions and system responses are as follows:

Descriptive question: What happened?
  System response: A person has congested lungs.
Diagnostic question: Why did it happen?
  System response: The person contracted a virus that damages the lungs and creates a fluid discharge that fills the lungs.
Predictive question: What will happen?
  System response: If the person does not stop the viral activity to inhibit the damage to the lungs and clear the fluid the person will likely die.
Prescriptive question: What should be done?
  System response: Drugs should be administered to kill the virus and all people exposed to the patient should be given an antiviral drug blocking the virus.

DETAILED DESCRIPTION

Figure 1:
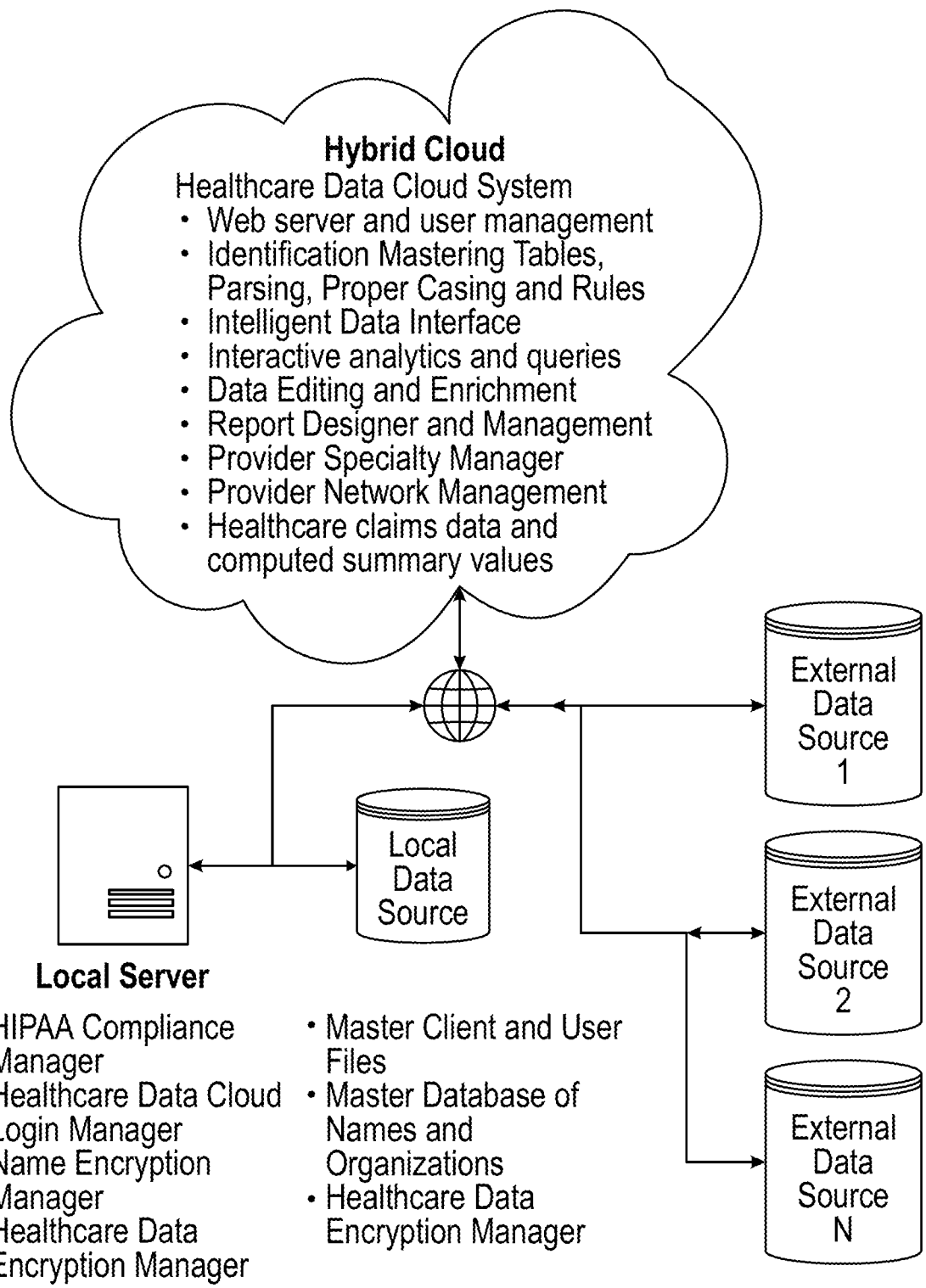
FIG. 1 illustrates a flow chart of a hybrid cloud system according to some embodiments.

FIG. 1 illustrates a flow chart of a hybrid cloud system according to some embodiments. In some embodiments, the Healthcare Data Cloud System (HDC; the system) operates in a hybrid cloud environment. In some embodiments, the healthcare data cloud system's application can scale efficiently for rapid growth. In some embodiments, the system uses conventional cloud services (e.g., Microsoft Azure, Amazon Web Services, etc.) In some embodiments, hybrid cloud architecture is designed to incorporate external computers, disk arrays and other cloud environments. In some embodiments, the system can access large troves of healthcare data without migrating to the cloud until usage volume requires a move to the cloud.

Figure 2:
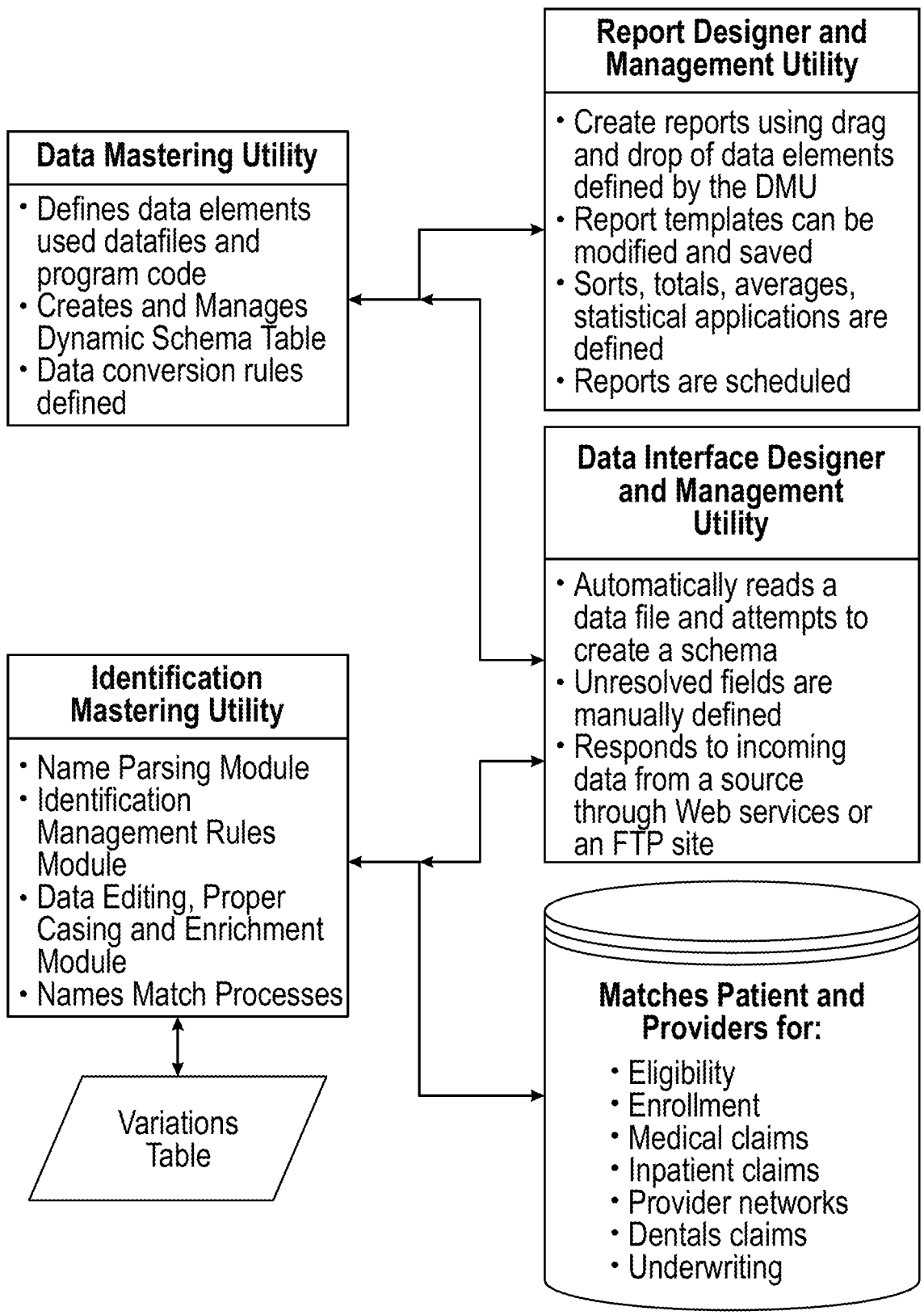
FIG. 2 illustrates a flow chart of the system's operations according to some embodiments.
Figure 3:
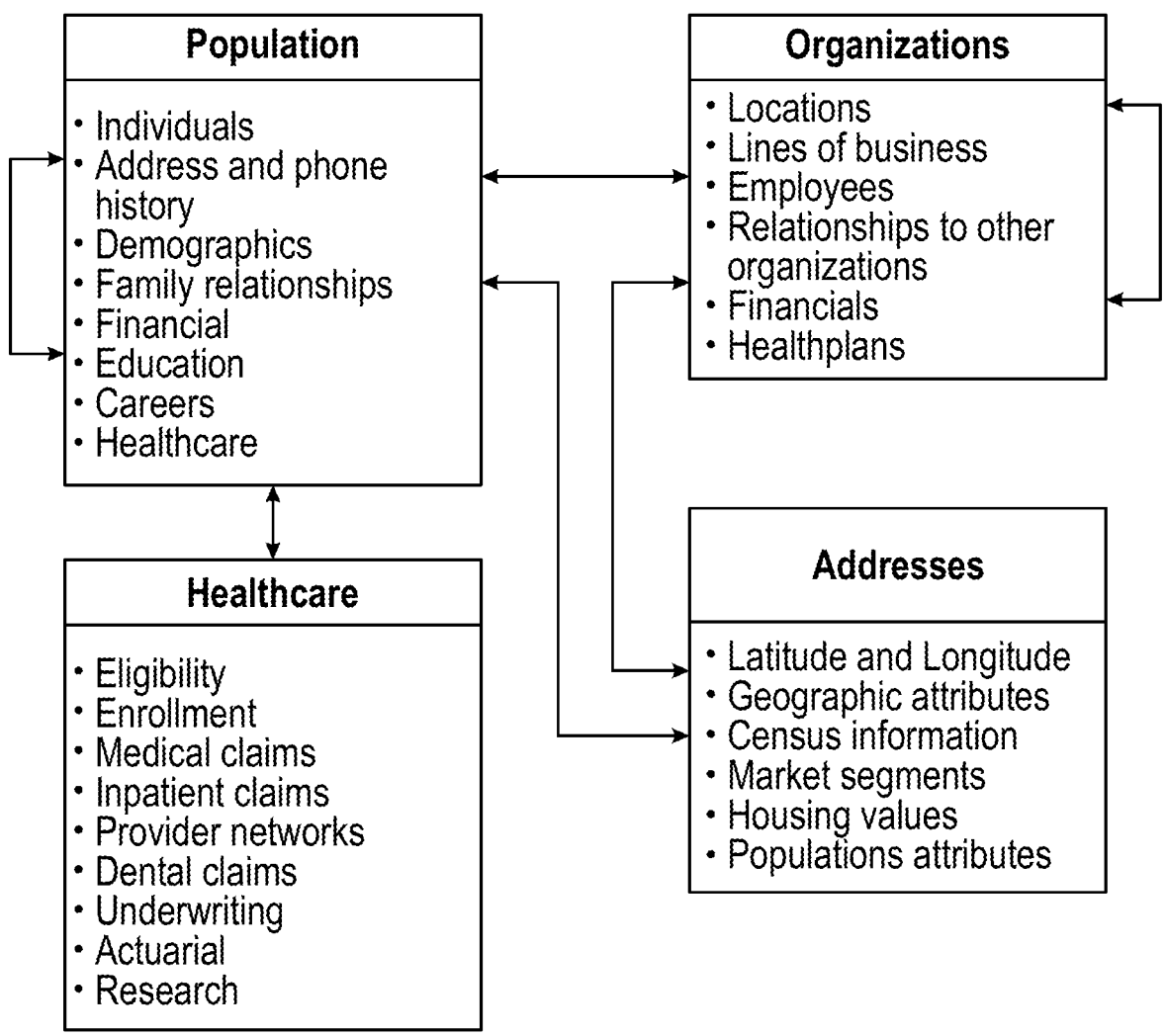
FIG. 3 illustrates a flow chart of Population, Organizations, Addresses and Healthcare Tables according to some embodiments.

FIG. 2 illustrates a flow chart of the system's operations and components according to some embodiments. In some embodiments, the system includes an Identification Mastering Utility (IMU); a Data Mastering Utility (DMU); a Report Designer Management Utility (RDMU); and a Data Interface Designer and Management Utility (DIDMU). In some embodiments, the arrows represent a bi-directional flow of data between each utility.

In some embodiments, the Identification Mastering Utility (IMU) includes tables that store multiple ID variations. In some embodiments, the IMU uses different tables for different ID types. In some embodiments, different ID types are stored in at least one of a Population Table, an Organization Table, and Address Table, and/or a Variations Table. In some embodiments, the system accesses one or more tables, utilities, and or modules described herein intermittently, consecutively, and/or simultaneously (simultaneously as used herein can include lag and or latency times associated with a conventional computer attempting to process multiple types of data at the same time).

In some embodiments, the system includes a Population Table. In some embodiments, the Population Table includes data on individuals in a geographical area. In some embodiments, a Population Table includes data on individuals in a country and/or in multiple countries. In some embodiments, the geographical area is used as an identifier.

In some embodiments, the system includes an Organization Table. In some embodiments, the Organization Table links an individual's data to an agency. In some embodiments, the Organization Table links an individual's data to multiple agencies. In some embodiments, agencies are used as an identifier.

In some embodiments, the system includes an Address Table. In some embodiments, in some embodiments, the Address Table links an individual's data to an address. In some embodiments, the Address Table links an individual's data to multiple addresses. In some embodiments, addresses are used as a unique identifier.

In some embodiments, the system includes one or more Variations Tables (a reference to a single Variations Table and/or multiple Variations Tables are collectively referred to as a/the Variations Table herein; a reference to a "table" is a refence to a table other than the Variations Table unless stated otherwise; a reference to a "table" may include any table that is part of the system and/or located in a separate database as described herein). In some embodiments, the Variations Table includes data variations from or more other tables. In some embodiments, each table has a corresponding Variations Table. In some embodiments, data variation from multiple tables are stored in a single Variations Table. In some embodiments, multiple Variations Tables include data from a single table. In some embodiments, a Variations Table includes any ID variations associated with an individual. As used herein, "table" includes any conventional data presentation format.

In some embodiments, example ID variations including name spellings (including misspellings), addresses, phone numbers or any ID describing an individual, and/or the error associated with the IDs. For example, Table 1 shows a Variations Table including variations of and ID for an individual Mary Jane Smith Jones, MD, according to some embodiments. In some embodiments, each numbered row corresponds to an ID used by one or more organizations. In some embodiments, the bracketed ID in row 1 is a master ID. In some embodiments, all IDs bolded and underlined in the Variations Table refer to the same individual: most ID variations have correct spellings but the underlined ID variations are errors.

TABLE 1

Variations Table

| No | First | Middle | Last | Degree |
|---|---|---|---|---|
| [1] | [Mary Jane] | | [Smith Jones] | [MD] |
| 2 | Mary | Jane | Smith-Jones | MD |
| 3 | Mary Jane | Smith | Jones | MD, PhD |
| 4 | Mary | | Jones | PA, PhD |
| 5 | Jane | | Smith | MD |
| 6 | Mary | Jones | Smith | |
| 6 | Jayne | | Smith | MD |
| 7 | Mary | Joan | Smyth | |
| 8 | MJ | Smith | Jones-Smith | PhD, MBA |
| 9 | MJ | | Smith | |

The IMU accumulates variations in IDs (e.g., names, addresses, titles, degrees, phone numbers, labels, personal attributes, organizational relationships and any other data elements from one or more agencies) and stores them in the Variations Table according to some embodiments. In some embodiments, the ID variations are ranked and labeled by frequency, accuracy, date entered, and ID currently used. In some embodiments, the highest ranked ID is labeled as a master ID. In some embodiments, one or more records associated with each ID variation is also associated with the master ID. In some embodiments, entry of any ID variation from the Variations Table causes the system to form links to data associated with the master ID (e.g., hospital records, criminal records, etc).

In some embodiments, each ID includes one or more data elements. In some embodiments, example data elements are shown in Table 3.

TABLE 3

Example Data Elements

| | Data Elements |
|---|---|
| 1. | HDCS_PERSONAL_ID |
| 2. | TELEPHONE NUMBER |
| 3. | TIME ZONE PHONE |
| 4. | MOBILE NUMBER |
| 5. | GENDER CODE |
| 6. | DOB_YR |
| 7. | DOB_MO |
| 8. | DOB_DY |
| 9. | AGE CALCULATED |
| 10. | AGE ESTIMATED |
| 11. | INCOME - ESTIMATED HOUSEHOLD |
| 12. | NET WORTH |
| 13. | EDUCATION |
| 14. | OCCUPATION |
| 15. | BUSINESS OWNER |
| 16. | NUMBER OF CHILDREN |
| 17. | PRESENCE OF CHILDREN |
| 18. | MARITAL STATUS IN THE HHLD |
| 19. | HOME OWNER or RENTER |
| 20. | LENGTH OF RESIDENCE |
| 21. | DWELLING TYPE |
| 22. | NUMBER OF ADULTS |
| 23. | HOUSEHOLD COUNT |
| 24. | HOME MARKET VALUE |

TABLE 3-continued

Example Data Elements

Address Data Elements

| | |
|---|---|
| 1. | HDCS_ADDRESS_ID |
| 2. | ADDRESS |
| 3. | ADDRESS_NO |
| 4. | ADDRESS_ST_NAME |
| 5. | ADDRESS_ST_TYPE |
| 6. | ADDRESS_VANITY |
| 7. | SUITE OR APT |
| 8. | CITY |
| 9. | STATE |
| 10. | ZIP5 |
| 11. | ZIP4 |
| 12. | DELIVERY POINT BAR CODE |
| 13. | CARRIER ROUTE |
| 14. | FIPS STATE CODE |
| 15. | FIPS COUNTY CODE |
| 16. | LATITUDE - rooftop level |
| 17. | LONGITUDE - rooftop level |
| 18. | ADDRESS TYPE INDICATOR |
| 19. | MSA CODE |
| 20. | CBSA CODE |
| 21. | ADDRESS LINE |
| 22. | CENSUS TRACT |
| 23. | CENSUS BLOCK GROUP |
| 24. | CENSUS BLOCK |
| 25. | CENSUS MEDIAN HOME VALUE |
| 26. | CENSUS MEDIAN HOUSEHOLD INCOME |
| 27. | TELEPHONE PRESENT FLAG |
| 28. | TELEPHONE NUMBER |
| 29. | TIME ZONE |

In some embodiments, the IMU includes a Name Parsing Module (NPM). In some embodiments, the NPM parses an ID from rows in one or more tables (e.g., the Variations Table) into one or more columns using an ID vector (IDV; also called a name vector). In some embodiments, instead of a name being stored in data fields such as First, Middle, Last names, names are stored in a name vector where names, spaces, and hyphens associated with an ID are stored with notation of the order. In some embodiments, matching logic is applied to the vector comparing it to all similar names in the Variations table and finding all possible matches. In some embodiments, additional data is then used to resolve the matches to one or a few choices. In some embodiments, the ID vector adds common and/or defined ID variations (e.g., names, spaces, hyphens, surname order, language-specific spellings, known misspellings, and/or punctuations) automatically to each ID and/or data element entered into the system as an ID iteration in one or more Variations Tables (e.g., a row in Table 1) and/or other tables.

In some embodiments, the system is configured to apply name match logic. In some embodiments, name match logic includes the application of a set a set of rules that utilizes the variations tables for individual names and organizations, addresses and IDs. In some embodiments, the logic table is derived by utilizing artificial intelligence routines to create 300 plus rules that utilize the tables which creates logical choices used to match names, organizations, addresses, claims, medical reports, etc. In some embodiments, NPM accesses one or more tables and applies the NMS steps described below.

TABLE 2

Name Matching Sequence
Name Match Sequence (NMS)

| | |
|---|---|
| 1. | Parse ID using ID vector |
| 2. | Match parsed ID to master ID |
| 3. | Match parsed ID to alternative names |
| 4. | Apply name match logic. |
| 5. | Accesses name finder web sites and match logic |
| 6. | Accesses 1 to 3 of the retail credit agencies and match logic |
| 7. | Collect IDs found on the web and found by phone calls and/or other communications and record those IDs along with ID manual edits in the Variations Table |

For example, with reference to Table 1, in some embodiments a primary name shown is Mary Jane Smith Jones. However, the name Mary Jane Smith Jones could appear in the Variations Table in any combination according to some embodiments. In some embodiments, the NPM can loop through the Name Match Sequence several times and apply some or all combination of IDs a and/or data elements in each row to get a table that includes columns representing each ID a and/or data element component (e.g., first name, last name, address, etc). In some embodiments, the system uses artificial intelligence (AI) to determine each ID and/or data element component data type. In some embodiments, each ID and/or data element component type is listed under a different field.

In some embodiments, the system includes a Data Editing, Proper Casing and Enrichment Module (DEPCEM) configured to be used by the IDM. In some embodiments, the DEPCEM is configured to create and incorporate edit tables. In some embodiments, the DEPCEM is configured to standardize data so that identification matches and statistical analyses function properly. In some embodiments, the DEPCEM includes tables such as titles, degrees and suffix (Jr, II, III, IV), Scottish names, proper casing and the like, ensure a standard approach to spelling. In some embodiments, the DEPCEM includes tables that include abbreviations such as degrees (i.e., PhD, MA, DO, MD), (Jr, III, IV), numbers and math symbols, proper formats for currencies, numbers formatting, and data standardization software. In some embodiments, the DEPCEM is configured to fill in missing data-dictionary entries based on a set of user or administrator defined rules. In some embodiments, the DEPCEM is configured to be editable to help ensure that names are properly identified and matched.

In some embodiments, the system uses the ID iterations to search for an individual's data and/or records across one or more organizations. In some embodiments, ID iterations are automatically associated with the master ID. In some embodiments, searching and or entering an ID that matches an ID iteration also returns all data associated with the master ID.

In some embodiments, the system includes one or more tables for one or more individual types. In some embodiments, the system includes a Population Table. In some embodiment, the Population Table includes names, records, and/or data elements of people residing and/or who have resided in the United States and/or any foreign country. In some embodiment, the Population Table holds over 300 million individual records of the 330 million total records in the United States. In some embodiments, the system is configured to be scalable to hold all records worldwide. In some embodiments, the Population Table can maintain one or more of the following data for each person: name, name variations (as created by the IMU); addresses, address variations (e.g., with 29 or more or fewer data elements for each address); personal data (e.g., with 20 or more or fewer data elements); retail credit and purchasing preferences (e.g., with 150 data elements); and/or ancillary data obtained from the internet. In some embodiments, a Population Table can include and/or link to one or more Variations Tables that includes ID and/or variations for each individual.

In some embodiments, the system includes an Organizations Table. In some embodiments, the Organizations Table holds the names, records, and/or data elements associated with one or more organizations (i.e., agencies). In some embodiments, the Organizations Table can hold over 20 million master records. In some embodiments, individuals can be linked to organizations. In some embodiments, organizations can include one or more of the following: companies, partnerships, social societies, practices, health plans, groups of individuals, clubs, associations and/or any type or agency. Some embodiments can include any number of data elements (e.g., addresses, telephone numbers, related individuals, organization health plans, related organizations, descriptive codes, services, web links, and/or anything that is associated with an individual the can be described in writing and/or digitally). In some embodiments, there are approximately 60 data elements for organizations. In some embodiments, organizations can be related to other organizations using artificial intelligence and/or statistical analyses techniques.

In some embodiments, the system includes an Organization Abbreviation Table. In some embodiments, organizations (i.e., agencies) present a more complex identification problem because they contain name variations and abbreviations. In some embodiments, an Organization Abbreviation Table can provide additional name variations. In some embodiments, the Organization Abbreviation Table can provide more data points such as multiple addresses, provider affiliations, organizations members, group affiliations, and the like. In some embodiments, the Organization Abbreviation Table can be utilized to accurately and precisely identify an organization.

Some embodiments of the system comprise an Address Table. In some embodiments, the Address Table holds the names, records, and/or data elements associated with one or more Addresses. In some embodiments, the Address Table can hold over 135 million master records. In some embodiments, one or more Variations Tables are configured to store the variations and/or the source of the variations. In some embodiments, one or more Variations Tables include one or more address data elements.

Some embodiments include a Dynamic Schema Table. In some embodiments, the Dynamic Schema Table can include extensible attributes. In some embodiments, a Data Interface and Management Utility and Report Designer is configured to use one or more Dynamic Schema Table definitions to determine how to format a field in a report.

TABLE 4

Dynamic Schema Table

| Function | Field Attributes | Use | Example | Alternatives |
|---|---|---|---|---|
| Variable | Field Name (Identifiers) | Alternative Field Names are retained | Provider Network Name | Provider Network Name (this is a table of alternative names) |
| Variable | Data Source | Data Source stores Field Name label alternatives | Net Table 10045A | Prov_Net_Name |
| Field Def | Field Size | Programmer definition | 50 | Prov Net Nm |
| Field Def | Input Mask | System function | | PNM |
| Value Def | Default Value | Used if no value found in incoming data | | Network Name |
| Value Def | Unit Measure | i.e. Source in Meters; Euros; Celsius | | Net Nm |
| Value Def | Unit Conversion | Converts to Feet; Dollars; Fahrenheit | | |
| Value Def | Converted Value | Converted value; system retains sample of data and creates a reference profile | | |
| Value Def | Validation Rule | Applied rules make sure values entered are valid | | |
| Value Def | Required | User left blank | M or F is required | |
| Value Def | Allow Zero Length | No entry required | | |
| Index | Indexed | System function | Yes | |
| Report | Minimum Value | User entered 3 | 5 | |
| Report | Maximum Value | User entered 50 | 20 | |
| Report | Unit of Measure | i.e. Feet or Meters | | |
| Report | Col Data Value | | | |
| Report | Report Col Label Short | User entered | Prov Nt Nm | |
| Report | Report Col Label Long | User entered | Prov Net Name | |
| Report | Column Width | Programmer definition | 30 | |
| Report | Default Sort | Programmer definition | Alpha A-Z | |

Some embodiments include a Data Interface and Management Utility (DIMU). In some embodiments, the DIMU can record field identifiers from any data source and map them to the master identifiers. In some embodiments, the DIMU can scan a healthcare data file. In some embodiments, the DIMU can attempt to define the data elements and create a schema (e.g., a Dynamic Schema Table) including field labels. In some embodiments, any unresolved field can be resolved manually. In some embodiments, the system can remember the edit definitions for the data source and can check for changes or errors in the data for all future loads.

In some embodiments, the system can automatically build a crosswalk table. In some embodiments, the crosswalk table is configured to automatically update changes to data (i.e. the system remembers (i.e., stores, accesses, and retrieves) a client's administrative system's tables of providers and member eligibility and can automatically update the client records (and one or more tables) when a change is recorded in the system.

In some embodiments, the DIMU can include data definition templates. In some embodiments, the data definition templates can be included for one or more of: provider networks, claims tables for medical, laboratory, hospital, eligibility, dental and electronic medical records in key systems. In some embodiments, one or more templates can be altered and saved as a new template.

Some embodiments include a Data Mastering Utility (DMU). In some embodiments, the DMU can describe any data element. In some embodiments, the data element is in one or more databases, tables and/or programs. Some embodiments include schema, such as field name or variable name, format, data type, size and other database attributes. In some embodiments, one or more field labels from any data source can be linked to the system field name. In some embodiments, data translation attributes can be specified between a data source and the healthcare data cloud system. In some embodiments, translation attributes allow data conversion to be applied automatically (i.e. meters to feet, kilograms to pounds, and the like, as a non-limiting examples).

Some embodiments include a Report Designer and Report Manager Utility (RDMU). In some embodiments, the RDMU is configured to allow users to drag-and-drop data elements defined in the DMU. In some embodiments, the schema for a data element contains a column width and column label. In some embodiments, the columns are distributed across a page and/or automatically formatted for portrait or landscape formats. In some embodiments, column totals and averages can be specified for each column. In some embodiments, running averages and other computational columns can be inserted along with titles and explanatory text, dates and times.

In some embodiments, the RDMU can include report templates. In some embodiments, the report templates can be used for one or more record of a database (e.g., provider networks, medical facilities, laboratories, hospitals, and dentist). In some embodiments, one or more templates are configured to be altered and saved as a new template. In some embodiments, the RDMU is configured to schedule report frequency and/or distribution.

The system includes a Provider Network Management System (PNMS) in some embodiments. In some embodiments, providers are mapped to any number of provider networks. In some embodiments, provider networks are defined by state and county or city. In some embodiments, subcontracted networks are defined to extend geographic coverage. In some embodiments, wrap around networks, out of area networks and specialty networks are defined and linked to a health plan. In some embodiments, the PNMS is configured to create networks. In some embodiments, the created networks are based on geography, specialty and subspecialty. In some embodiments, PNMS is configured to create model networks that are tested against patient distribution and coverage for each patient by specialty. In some embodiments, the PNMS is configured to model financial performance when data is available.

In some embodiments, the PNMS is configured to define a model network. In some embodiments, the model network is comprised of any number of contracted PPO networks by using states or counties to specify the geographic area covered by each network. In some embodiments, the model network is refined by provider category (i.e. medical, dental, vision, ancillary, and the like) and/or specialty (i.e. primary care, orthopedic, psychiatric, and the like). In some embodiments, individual facilities and/or physicians are included or excluded from a model network to meet exact provider network requirements.

In some embodiments, the PNMS includes a method of use that includes one or more of the following steps: define a model network to meet the requirements and needs of any organization or health plan; find doctors or hospitals contracted by their health plan by using a provider finder web site that accesses the specific provider network assigned to their health plan; automatically transmit a provider network data set to each payer client for use in the claims system of a provider network; access a payer client claims system plan's specific network through a web service to get up-to-date validation of provider network status; use a web service for a payer client to "identify" the provider in a claim and obtain up-to-date demographic and billing information; and/or use a web service to determine if a provider is in or out of network on a specific date.

Some embodiments can include a Provider Specialty Management Module (PSMM). In some embodiments, the specialty manager table can incorporate cross-reference technology. In some embodiments, the cross-reference technology is configured to automatically create one or more provider types, specialties, and/or subspecialty categories for any client, in any country, and/or in any common languages. In some embodiments, cross-reference technology includes the system being configured to use the specialty (and/or specialties) claimed by the healthcare provider and matches the claims to actual diagnoses, procedures and prescriptions issued by the provider and determine if the provider's practice patterns support the claimed specialties.

Some embodiments include a Health Insurance Portability and Accountability Act (HIPPA) compliance module. In some embodiments, the HIPAA compliance module is configured to identify a patient, validate the provider's right to review the patient's medical records, and/or record that the provider did attest to the patient signing the HIPAA release. In some embodiments, the system is configured to store a copy of the patient release. In some embodiments, the HIPPA compliance module is configured to allow a provider to upload documents including the HIPAA release. In some embodiments, the system is configured to text the patient's phone and obtain a text confirmation of the patient's agreement to release the healthcare records to the provider.

Some embodiments of the system include a Data Security and Encryption Module (DSEM). In some embodiments, all HIPAA data is retained in separate, secure data areas and related to each of the system modules through encrypted keys. In some embodiments, key identifiers are encrypted and retained in secure data areas. In some embodiments, user logins are managed through a system identifier that utilizes numerous data elements to identify users and their compliance with HIPAA rules.

Figure 4:
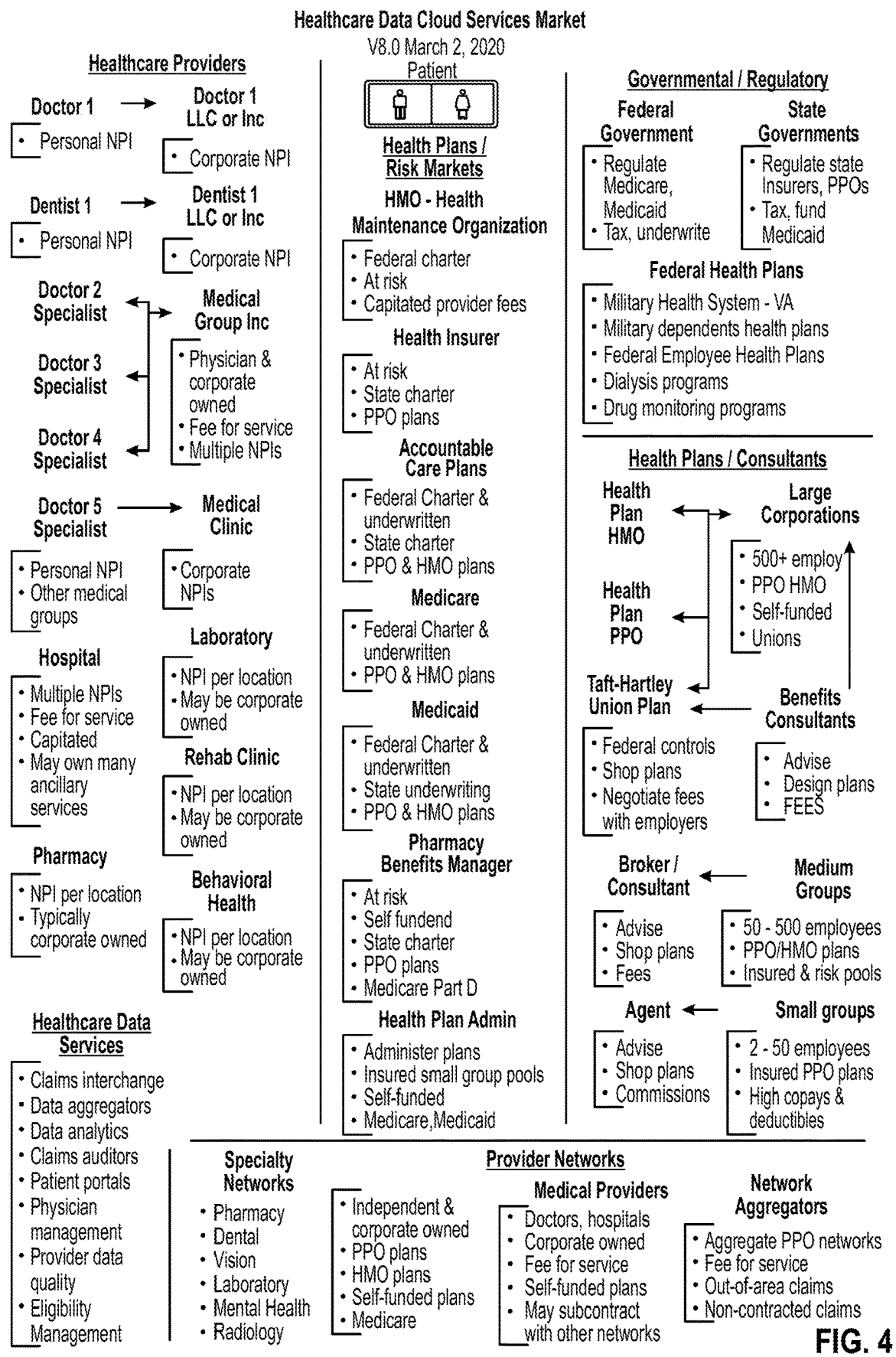
FIG. 4 illustrates an example service market the system is configured to support according to some embodiments.

As shown in FIG. 4, in some embodiments the system (i.e., the Healthcare Data Cloud System; HDC) supports a market that includes a vast array of organizations that are designing, underwriting and offering health plan models. In some embodiments, numerous organizations that offer patient medical services; that administer claims and audit and analyze claims. In some embodiments, the system provides a web-based service to all healthcare organizations to correlate identifiers, data elements, and/or records associated with an individual a single global HDC identifier. In some embodiments, approximately 300 million people are covered by health plans, but everyone uses the healthcare system and almost all of healthcare are subsidized. FIG. 4 shows many types of healthcare providers and support organizations and all of them maintain their own patient and plan-member identifiers. In some embodiments, the system is configured to create a data model for each type of healthcare organization represented in FIG. 4.

In some embodiments, the healthcare data cloud services market depicted in FIG. 4 is shown as an active web page in the system. In some embodiments, each organization type such as individuals, organizations, insurers, HMO's medical groups, reinsurers, provider networks, etc. require different types of information for operations and decision-making purposes. In some embodiments, by clicking on an organization type on the market web page the user defines the data requirements for accepting data from and delivering data to that organization. Also, in some embodiments, the organization variations table includes retention models for deriving profitability, utilization, patient mix, high-risk patients and many other factors important to the business of healthcare stored with the organizations profile. In some embodiments, the system is configured to manage the data communications between a physician specialty group and an insurance plan administrator just by clicking on the diagram location for both organizations in the active web page depicted in FIG. 4.

Figure 5:
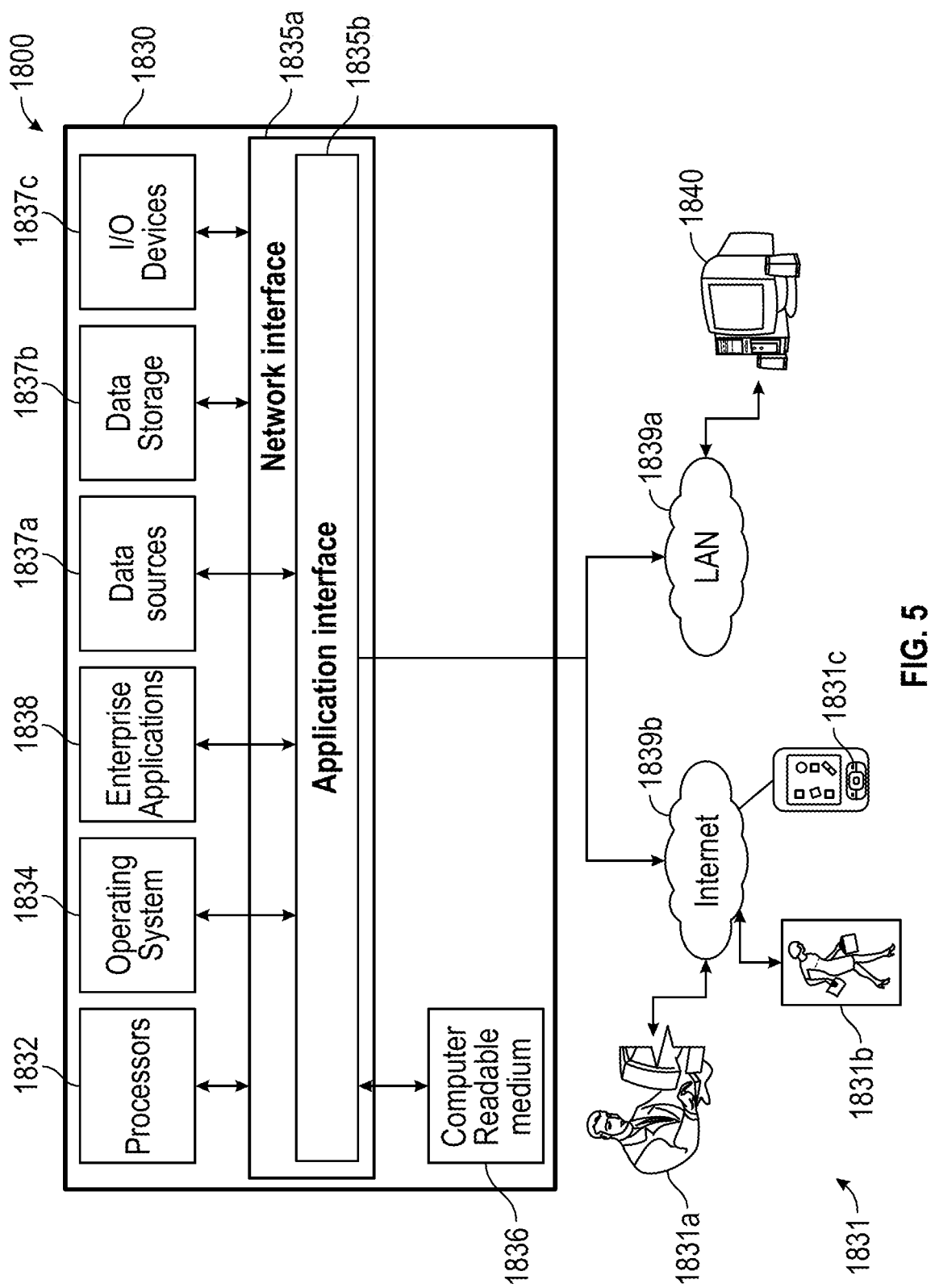
FIG. 5 illustrates a computer server system network in communication with the system according to some embodiments.

FIG. 5 illustrates a computer server system network 1830 of the system's content control server system architecture according to some embodiments of the invention. In some embodiments, the computer server system network 1830 comprises a computer server system 1830 configured for operating and processing components of the content control server system architecture 10 in accordance with some embodiments of the invention. In some embodiments, the computer system 1830 is configured to process one or more software modules of the aforementioned content control system and method applications and is configured to display information related to user content within one or more graphical user interfaces. In some embodiments, the server system 1830 is configured to comprise at least one computing device including at least one processor 1832. In some embodiments, the at least one processor 1832 is configured to include a processor residing in or coupled to one or more server platforms. In some embodiments, the server system 1830 is configured to include a network interface 1835a and an application interface 1835b coupled to the least one processor 1832 is configured to be capable of processing at least one operating system 1840. Further, in some embodiments, the interfaces 1835a, 1835b coupled to at least one processor 1832 can be configured to process one or more of the software modules (e.g., such as enterprise applications 1838). In some embodiments, the software modules 1838 can include server-based software that is configured to include content control software modules such as a content engine. In some embodiments, the software modules 1838 is configured to operate to host at least one user account and/or at least one client account and operate to transfer data between one or more of these accounts using the at least one processor 1832, and process any operation of the content control server system architecture 10 described herein.

With the above embodiments in mind, it should be understood that the invention can employ various computer-implemented operations involving content control data stored in computer systems according to some embodiments. Moreover, in some embodiments, the above-described databases and models throughout the content control can store analytical models and other data on computer-readable storage media within the server system 1830 and on computer-readable storage media coupled to the server system 1830. In addition, in some embodiments, the above-described applications of the content control system 10 can be stored on computer-readable storage media within the server system 1830 and on computer-readable storage media coupled to the server system 1830. In some embodiments, these operations are those requiring physical manipulation of physical quantities. 'Usually, though not necessarily, in some embodiments these quantities take the form of electrical, electromagnetic, or magnetic signals, optical or magneto-optical form capable of being stored, transferred, combined, compared and otherwise manipulated. In some embodiments, the server system 1830 is configured to comprise at least one computer readable medium 1836 coupled to at least one data source 1837a, and/or at least one data storage device 1837b, and/or at least one input/output device 1837c. In some embodiments, the invention is configured to be embodied as computer readable code on a computer readable medium 1836. In some embodiments, the computer readable medium 1836 is configured to be any data storage device that can store data, which can thereafter be read by a computer system (such as the server system 1830). In some embodiments, the computer readable medium 1836 is configured to be any physical or material medium that can be used to tangibly store the desired information or data or instructions and which can be accessed by a computer or processor 1832. In some embodiments, the computer readable medium 1836 is configured to include hard drives, network attached storage (NAS), read-only memory, random-access memory, FLASH based memory, CD-ROMs, CD-Rs, CD-RWs, DVDs, magnetic tapes, other optical and non-optical data storage devices. In some embodiments, various other forms of computer-readable media 1836 is configured to transmit or carry instructions to a computer 1840 and/or at least one user 1831, including a router, private or public network, or other transmission device or channel, both wired and/or wireless. In some embodiments, the software modules 1838 is configured to send and receive data from a database (e.g., from a computer readable medium 1836 including data sources 1837a and data storage 1837b that can comprise a database), and data can be received by the software modules 1838 from at least one other source. In some embodiments, at least one of the software modules 1838 is configured to output data to at least one user 1831 via at least one graphical user interface rendered on at least one digital display.

In some embodiments, the computer readable medium 1836 is configured to be distributed over a conventional computer network via the network interface 1835a where the content control system 10 embodied by the computer readable code can be stored and executed in a distributed fashion. For example, in some embodiments, one or more components of the server system 1830 are configured to be coupled to send and/or receive data through a local area network ("LAN") 1839*a* and/or an Internet coupled network 1839*b* (e.g., such as a wireless Internet). In some embodiments, the networks 1839*a*, 1839*b* are configured to include wide area networks ("WAN"), direct connections (e.g., through a universal serial bus port), or other forms of computer-readable media 1836, and/or any combination thereof.

In some embodiments, components of the networks 1839*a*, 1839*b* are configured to include any number of user devices such as personal computers including for example desktop computers, and/or laptop computers, or any fixed, generally non-mobile Internet appliances coupled through the LAN 1839*a*. For example, some embodiments include personal computers 1840*a* coupled through the LAN 1839*a* that are configured for any type of user including an administrator. Some embodiments include personal computers coupled through network 1839*b*. In some embodiments, one or more components of the server system 1830 are configured to send or receive data through an Internet network (e.g., such as network 1839*b*). For example, some embodiments include at least one user 1831 coupled wirelessly and accessing one or more software modules of the content control system 10 including at least one enterprise application 1838 via an input and output ("I/O") device 1837*c*. In some embodiments, the server system 1830 can enable at least one user 1831 to be coupled to access enterprise applications 1838 via an I/O device 1837*c* through LAN 1839*a*. In some embodiments, the user 1831 is configured to comprise a user 1831*a* coupled to the server system 1830 using a desktop computer, and/or laptop computers, or any fixed, generally non-mobile Internet appliances coupled through the Internet 1839*b*. In some embodiments, the user 1831 can comprise a mobile user 1831*b* coupled to the server system 1830. In some embodiments, the user 1831*b* can use any mobile computing device 1831*c* to wireless coupled to the server system 1830, including, but not limited to, personal digital assistants, and/or cellular phones, mobile phones, or smart phones, and/or pagers, and/or digital tablets, and/or fixed or mobile Internet appliances.

In some embodiments, the server system 1830 is configured to enable one or more users 1831 coupled to receive, analyze, input, modify, create and send data to and from the server system 1830, including to and from one or more enterprise applications 1838 running on the server system 1830. In some embodiments, at least one software application 1838 running on one or more processors 1832 is configured to be coupled for communication over networks 1839*a*, 1839*b* through the Internet 1839*b*. In some embodiments, one or more wired or wirelessly coupled components of the network 1839*a*, 1839*b* is configured to include one or more resources for data storage. For example, in some embodiments, this can include any other form of computer readable media in addition to the computer readable media 1836 for storing information, and can include any form of computer readable media for communicating information from one electronic device to another electronic device.

Figure 6:
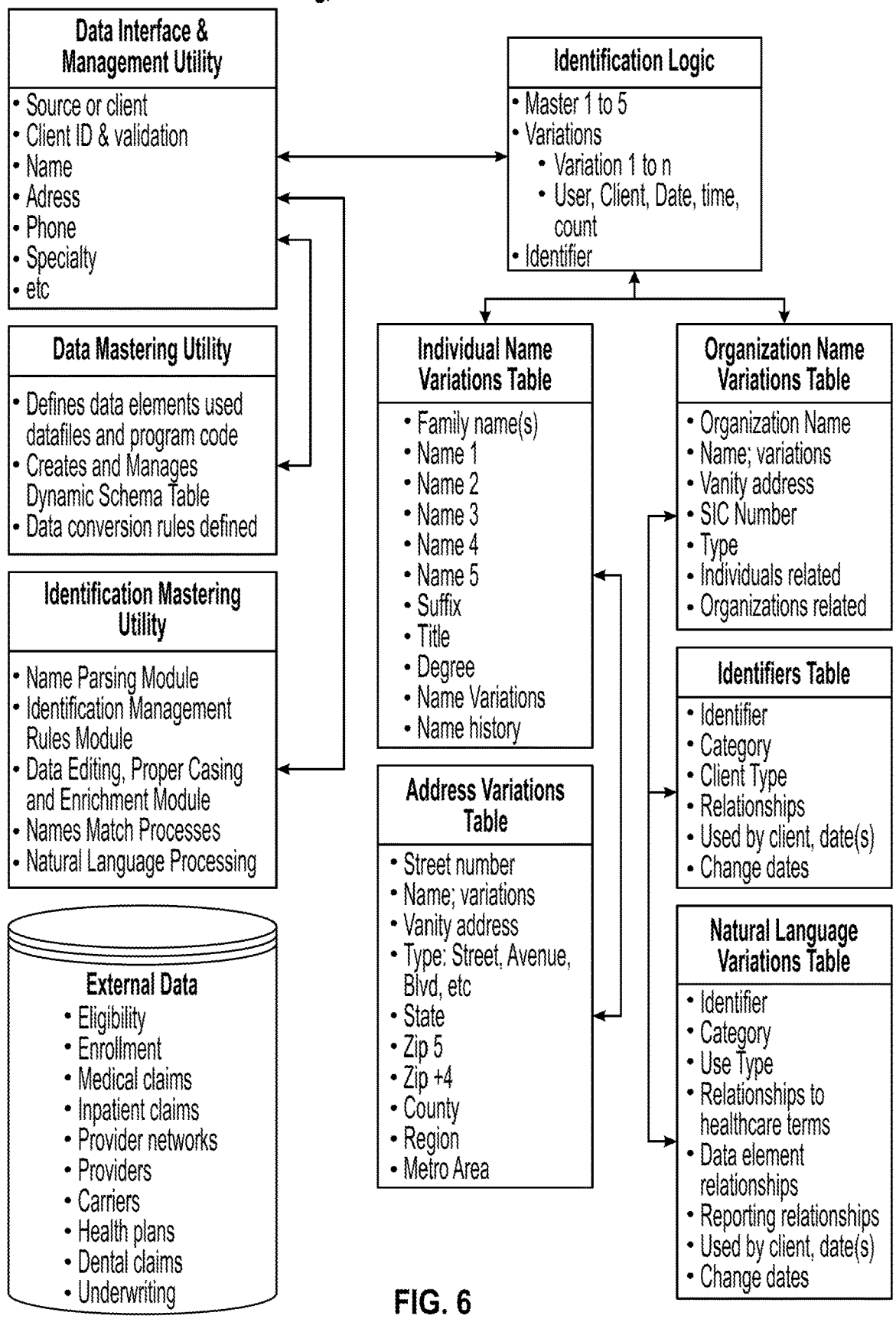
FIG. 6 illustrates another flow chart of the system's operations and components according to some embodiments.

FIG. 6 illustrates another flow chart of the system's operations and components according to some embodiments. In some embodiments, the system includes a Data Interference and Management Utility; a Data Mastering Utility; an Identification Mastering Utility; External Data collected from one or more external databases; Identification Logic; an Individual Name Variations Table; and Organization Name Variations Table; an Identifiers Table; and Address Variations Table; and/or a Natural Language Variations table. In some embodiments, the arrows represent a bi-directional flow of data between each utility.

It is understood that the invention is not limited in its application to the details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting.

The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Furthermore, acting as Applicant's own lexicographer, Applicant defines the use of and/or, in terms of "A and/or B," to mean one option could be "A and B" and another option could be "A or B." Such an interpretation is consistent with ex parte Gross, where the Board established that "and/or" means element A alone, element B alone, or elements A and B together.

Some embodiments of the system are presented with specific values and/or setpoints. These values and setpoints are not intended to be limiting and are merely examples of a higher configuration versus a lower configuration and are intended as an aid for those of ordinary skill to make and use the system. In addition, "substantially" and/or "approximately" when used in conjunction with a value encompass a difference of 10% or less of the same unit and scale of that being measured. In some embodiments, "substantially" and/or "approximately" are defined as presented in the specification.

The description is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown but are to be accorded the widest scope consistent with the principles and features disclosed herein. The detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data can be obtained over a network the data can be processed by other computers on the network, e.g. a cloud of computing resources.

Some embodiments of the present invention can be defined as a machine that transforms data from one state to another state. In some embodiments, the data can represent an article, that can be represented as an electronic signal and electronically manipulate data. The transformed data can, in some cases, be visually depicted on a display, representing the physical object that results from the transformation of data. In some embodiments, the transformed data can be saved to storage generally or in particular formats that enable the construction or depiction of a physical and tangible object. In some embodiments, the manipulation can be performed by a processor.', the processor thus transforms the data from one thing to another. Still further, in some embodiments, the methods can be processed by one or more machines or processors that can be connected over a network. In some embodiments, each machine can transform data from one state or thing to another, and can also process data, save data to storage, transmit data over a network, display the result, or communicate the result to another machine. In some embodiments, computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way according to some embodiments.

The invention claimed is:

1. A system comprising:
   one or more computers comprising one or more processors and one or more non-transitory computer readable media, the one or more non-transitory computer readable media storing instructions thereon that cause the one or more computers to:
   execute, by the one or more processors, an association between a Variations Table and an Identification Mastering Utility, the Variations Table comprising software configured to store one or more variations of one or more identifiers, the Identification Mastering Utility comprising software configured to process the one or more variations of the one or more identifiers;
   receive, by the Identification Mastering Utility, the one or more variations of the one or more identifiers, the one or more identifiers comprising names and/or numbers associated with an individual;
   store, by the Identification Mastering Utility, the one or more variations of the one or more identifiers into one or more tables within the Variations Table;
   send, by the Identification Mastering Utility, the one or more variations to a Name Parsing Module, the Name Parsing Module comprising software configured to parse the one or more variations of the one or more identifiers;
   parse, by the Name Parsing Module, each of the one or more variations into a vector, the vector comprising a notation of an order of names and spaces within each of the one or more variations; and
   execute, by the one or more processors, an association of one or more vectors to a record of the individual;
   wherein the Identification Mastering Utility is configured to return the record associated with the individual upon receiving an input comprising at least one of the one or more identifiers.

2. The system of claim 1,
   wherein the Identification Mastering Utility is configured to analyze the Variations Table and determine a most common iteration;
   wherein the Identification Mastering Utility is configured to assign the most common iteration as a master identifier; and
   wherein all identifiers associated with the individual are associated with the master identifier.

3. The system of claim 2,
   wherein each of the one or more identifiers comprise a plurality of data elements;
   wherein the Name Parsing Module is configured to parse each of the one or more identifiers stored in one or more rows into one or more columns; and
   wherein each of the one or more columns comprises at least one of the plurality of data elements.

4. The system of claim 1,
   wherein the Identification Mastering Utility is configured to search one or more databases;
   wherein the Identification Mastering Utility is configured to collect and/or store the one or more identifiers and/or one or more data elements associated with the individual; and
   wherein the Identification Mastering Utility is configured to store each of the one or more identifiers and/or the one or more data elements in one or more rows of the Variations Table.

5. The system of claim 4,
   wherein the Identification Mastering Utility is configured to analyze the Variations Table and determine a most common iteration;
   wherein the Identification Mastering Utility is configured to assign the most common iteration as a master identifier; and
   wherein all identifiers associated with the individual are associated with the master identifier.

6. The system of claim 3,
   wherein the one or more data elements comprise one or more of an address data element, a biometric data element, a phone number data element, and/or a geographical data element.

7. The system of claim 4,
   wherein the one or more data elements comprise one or more of an address data element, a biometric data element, a phone number data element, and/or a geographical data element.

\* \* \* \* \*